United States Patent
Meier et al.

(10) Patent No.: US 10,994,270 B2
(45) Date of Patent: May 4, 2021

(54) METHOD FOR REACTIVATION OF A HOMOGENEOUS OXIDATION CATALYST

(71) Applicant: Evonik Operations GmbH, Essen (DE)

(72) Inventors: Ralf Meier, Dortmund (DE); Stephanie Bajus, Hanau (DE); Jens Döring, Dortmund (DE)

(73) Assignee: Evonik Operations GmbH, Essen (DE)

( * ) Notice: Subject to any disclaimer, the term of this patent is extended or adjusted under 35 U.S.C. 154(b) by 193 days.

(21) Appl. No.: 16/312,173

(22) PCT Filed: Jun. 28, 2017

(86) PCT No.: PCT/EP2017/065957
§ 371 (c)(1),
(2) Date: Dec. 20, 2018

(87) PCT Pub. No.: WO2018/002114
PCT Pub. Date: Jan. 4, 2018

(65) Prior Publication Data
US 2019/0232271 A1    Aug. 1, 2019

(30) Foreign Application Priority Data
Jun. 30, 2016   (EP) .................................... 16177260

(51) Int. Cl.
*B01J 38/66*    (2006.01)
*B01J 38/64*    (2006.01)
(Continued)

(52) U.S. Cl.
CPC .............. *B01J 38/66* (2013.01); *B01J 23/30* (2013.01); *B01J 38/64* (2013.01); *C07C 45/58* (2013.01);
(Continued)

(58) Field of Classification Search
CPC ... B01J 38/66; B01J 23/28; B01J 23/30; B01J 38/64; C07C 45/58; C07C 249/08;
(Continued)

(56) References Cited

U.S. PATENT DOCUMENTS 2,869,986 A * 1/1959 Anderson ............. C07C 31/225
549/531
2,968,527 A * 1/1961 Baker .................... C01G 41/00
423/54
(Continued)

FOREIGN PATENT DOCUMENTS

DE    30 27 349    2/1981
EP    1 411 051    4/2004
(Continued)

OTHER PUBLICATIONS

Xin-Yan Wang et al., "Kinetics and mechanism on the epoxidation of cis-1-propenylphosphonic acid in H2O catalyzed by tungstate(VI) or molybdate(VI)." Journal of Molecular Catalysis A: Chemical 206, pp. 213-223. (Year: 2003).*
(Continued)

*Primary Examiner* — Patricia L. Hailey
(74) *Attorney, Agent, or Firm* — Grüneberg and Myers PLLC

(57) ABSTRACT

The present invention relates to a method for the reactivation of homogeneous catalyst systems from organic reaction mixtures. The catalyst systems are suitable for the oxidation of organic compounds such as, for example, cyclododecene. The reactivation is carried out using an aqueous base.

16 Claims, 2 Drawing Sheets

Figure 1:
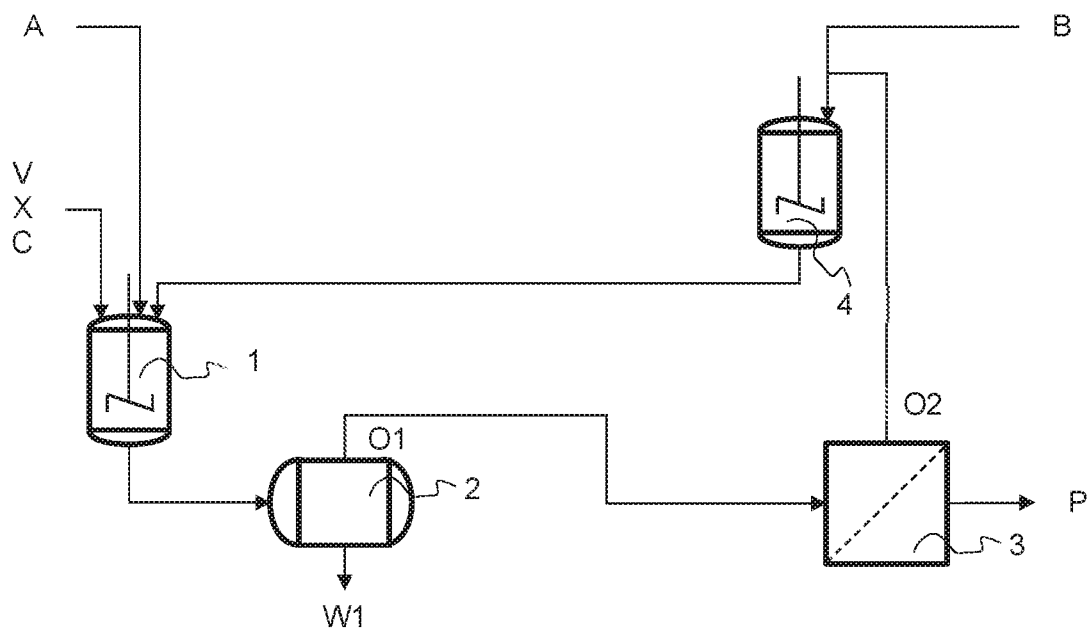

(51) Int. Cl.
*B01J 23/30* (2006.01)
*C07D 225/02* (2006.01)
*C07C 45/58* (2006.01)
*C07C 249/08* (2006.01)
*C07D 301/12* (2006.01)

(52) U.S. Cl.
CPC .......... *C07C 249/08* (2013.01); *C07D 225/02* (2013.01); *C07D 301/12* (2013.01); *C07C 2601/20* (2017.05); *Y02P 20/584* (2015.11)

(58) Field of Classification Search
CPC .............. C07C 2601/20; C07D 225/02; C07D 301/12; Y02P 20/584
USPC ............... 502/25, 26, 54, 85, 208, 210, 211, 502/305–306, 317
See application file for complete search history.

(56) References Cited

U.S. PATENT DOCUMENTS

| | | | |
|---|---|---|---|
| 3,231,329 A | | 1/1966 | Weiss et al. |
| 4,048,225 A | * | 9/1977 | Prescher .................. B01J 23/92 562/585 |
| 4,150,241 A | * | 4/1979 | Prescher .................. B01J 23/92 562/585 |
| 4,197,161 A | | 4/1980 | Friedrich et al. |
| 4,814,305 A | * | 3/1989 | Kamogawa ........... C07C 51/252 502/26 |
| 2004/0073051 A1 | | 4/2004 | Herwig et al. |
| 2015/0328619 A1 | | 11/2015 | Meier et al. |
| 2016/0031784 A1 | | 2/2016 | Micoine et al. |
| 2018/0155264 A1 | * | 6/2018 | Bajus .................... C07C 49/603 |

FOREIGN PATENT DOCUMENTS

| | | | | |
|---|---|---|---|---|
| EP | 2 946 831 | | 11/2015 | |
| EP | 2 980 069 | | 2/2016 | |
| GB | 894592 | | 4/1962 | |
| GB | 2 055 821 | | 3/1981 | |
| JP | 04-190851 | * | 7/1992 | .............. B01J 38/00 |
| TW | 2007-40522 | * | 11/2007 | .............. B01J 19/00 |
| WO | WO 00/44704 | | 8/2000 | |

OTHER PUBLICATIONS

International Search Report dated Sep. 19, 2017 in PCT/EP2017/065957.
Written Opinion dated Sep. 19, 2017 in PCT/EP2017/065957.
Chowdhury et al. "Recovery of Homogeneous Polyoxometallate Catalysts from Aqueous and Organic Media by a Mesoporous Ceramic Membrane without Loss of Catalytic Activity", Chem. Eur. J. 2006, 12, 3061-3066 DOI: 10.1002/chem.200501021.
Haimov et al "Alkylated Polyethyleneimine/Polyoxometalate Synzymes as Catalysts for the Oxidation of Hydrophobic Substrates in Water with Hydrogen Peroxide," J. Am. Chem. Soc. 2004, 126, 11762-11763 XP55330819A1.
Kamata et al. "Epoxidation of Alkenes with Hydrogen Peroxide Catalyzed by Selenium-Containing Dinuclear Peroxotungstate and Kinetic, Spectroscopic, and Theoretical Investigation of the Mechanism," Inorg. Chem. 2010, 49, 2471-2478 DOI: 10.1021/ic902381b.
Mizuno et al "Molecular design of selective oxidation catalyst with polyoxometalate," Catalysis Today, 117 (2006) 32-36 doi: 10.1016/j.cattod.2006.05.002.

* cited by examiner

METHOD FOR REACTIVATION OF A HOMOGENEOUS OXIDATION CATALYST

This application is a National Stage entry under § 371 of International Application No. PCT/EP2017/065957, filed on Jun. 28, 2017, and which claims the benefit of European Application No. 16177260,3, filed on Jun. 30, 2016, the entire contents of which are hereby incorporated by reference.

The present invention relates to a method for the reactivation of a homogeneous oxidation catalyst. Furthermore, the invention relates to a method for the oxidation of organic compounds. Moreover, the invention relates to a method for the synthesis of laurolactam and also nylon 12.

Cyclododecanone (CDON) is used for the synthesis of laurolactam. The lactam in turn is suitable for the preparation of nylon 12. The preparation of CDON may proceed from cyclododecatriene (CDT). First of all, a selective hydrogenation of cyclododecatriene (CDT) to cyclododecene (CDEN) may be undertaken. This is followed by an epoxidation of CDEN to monoepoxycydododecane (CDAN epoxide) and the rearrangement of CDAN epoxide to cyclododecanone (CDON).

The epoxidation of CDEN can be carried out, for example, in a biphasic system in the presence of a homogeneous catalyst system. According to EP-A-2946831 (US 2015/0328619), the epoxidized product is separated from the remaining reaction mixture on a membrane. The catalyst system remains in the retentate and can be recycled to the reaction mixture in the circuit as a continuous process.

In this context, it has however been observed that the conversion at a constant catalyst concentration decreases over the course of time. A decreasing conversion can be compensated by the feeding of fresh catalyst. Consequently it has been observed, particularly in continuous processes, that the catalyst progressively concentrates, in order to maintain a constant conversion. As a consequence, the catalyst converts into a less reactive species. Furthermore, the catalyst precipitates at many positions of the apparatus or system. The solid disrupts the reaction regime and blocks the membrane filter used.

The addition of new catalyst, however, has the disadvantage that the consumption of catalyst increases. In addition to increasing costs, this leads especially to an increased burden on the environment.

The object now consisted of providing an improved method for the oxidation of organic compounds. In this context, the conversion of the organic compound used should be maintained as constant as possible. Furthermore, the amount of new catalyst should be in particular reduced, in order to sustainably avoid environmental pollution. Moreover, the formation of precipitated catalyst should be avoided.

Accordingly, a novel method according to claim 1 has been found which permits reactivation of the catalyst used. In this way, the amount of fresh catalyst can be reduced or fresh catalyst can be completely dispensed with. In the method, an unsaturated organic compound is oxidized in a reaction mixture to obtain an epoxidized product. The reaction mixture comprises a homogeneous catalyst system, which catalyses the oxidation of the organic compound, and at least one peroxide. The catalyst system comprises at least one metal in its highest oxidation state, wherein the metal is selected from at least one metal of the IVb, Vb and VIb groups of the periodic table. These especially include titanium (highest oxidation state: 4), zirconium (4), hafnium (4), vanadium (5), niobium (5), tantalum (5), chromium (6), molybdenum (6) and tungsten (6). In addition, at least one phosphorus derivative is included, preferably as an oxygen-containing acid. The catalyst system is reactivated by addition of at least one aqueous base at a pH≥4, preferably ≥4.5, preferably ≥7 and particularly preferably ≥11.

By means of the method according to the invention, it is possible to prevent the precipitation of the catalyst system. The concentration of the catalyst can be suppressed, wherein an equally high conversion can be achieved compared to the prior art.

Further configurations of the invention are found in the dependent claims.

In the context of the invention, oxidations include epoxidations. Epoxidations are preferred oxidations.

In the context of this invention, the term organic compounds is understood to mean compounds which comprise at least two carbon atoms, are linear or cyclic and may contain one or more double bonds. The organic compounds are unsaturated. The unsaturated organic compounds preferably comprise C=C double bonds, with preferably no triple bonds being present. Preference is given to unsaturated compounds having six to twelve carbon atoms, wherein these are particularly preferably cyclic, especially comprising C=C double bonds in each case. Especially preferred are cyclic unsaturated C12 compounds, more preferred are cyclic C12 compounds having C=C double bonds, particularly CDEN. CDAN epoxide is formed from CDEN by the reaction.

Suitable peroxides are known to those skilled in the art. These include 3-chloroperoxybenzoic acid, peroxybenzoic acid, peroxyacetic acid, peroxybenzimidic acid, tert-butylhydroperoxide, dimethyldioxirane, potassium hydrogen peroxomonosulphate and hydrogen peroxide, wherein hydrogen peroxide is preferred.

Suitable catalyst systems comprise transition metals, particularly tungsten, molybdenum or vanadium, such as are described in WO 00/44704 A1 (AU 2299400 A) or DE 3027349 A1 (GB 2055821 B). The catalyst system can be the catalytically active substance itself or a mixture with water or organic solvents. The organic compound can function as organic solvent.

The catalyst system comprises preferably a derivative of a metal which is selected from tungsten, molybdenum and vanadium. Useful derivatives include, for example, an oxide, a mixed oxide, an oxygen-containing acid, a salt of an oxygen-containing acid, a carbonyl derivative, a sulphide, a chloride, an oxychloride or an alkanoate of the elements tungsten, molybdenum and/or vanadium. Preference is given to salts of tungstic acid, more preferably alkali metal salts of tungstic acid, especially preferably Li, Na or K salts.

Suitable derivatives include, for example, the metal carbonyls $W(CO)_6$ or $Mo(CO)_6$, the oxides $MoO_2$, $MoO_5$, $Mo_2O_3$, $MoO_3$, $WO_2$, $W_2O_5$, $WO_3$, $VO_2$, $V_2O_3$ or $V_2O_5$ and the sulphides $WS_2$ or $WS_3$. Further examples include the oxoacids $H_2WO_4$ and $H_2MoO_4$ or the alkali metal and alkaline earth metal salts thereof. Existing epoxidation catalysts comprise, for example, tungstate or molybdate, in particular sodium tungstate $Na_2WO_4$ or sodium molybdate $Na_2MoO_4$. Furthermore, the metal of the catalyst system can be present as a polyoxometalate.

These compounds are usually converted into the catalytically active compound in situ. This is effected by reaction with a phosphorus derivative, as well as a silicon and/or arsenic derivative. Compounds particularly suitable therefor are oxides, oxoacids, salts of oxoacids, sulphides, chlorides, oxychlorides or fluorides of phosphorus, silicon and/or arsenic.

The catalyst system thus preferably comprises a catalytically active compound obtained by reacting a tungsten, molybdenum or vanadium derivative with a phosphorus and optionally silicon or arsenic derivative. In one especially preferred embodiment, the catalytically active transition metal compound is formed in situ by reaction of sodium tungstate with phosphoric acid.

In a particularly preferred embodiment of the present invention, the catalyst system accordingly comprises phosphoric acid and a derivative of a metal selected from tungsten, molybdenum and vanadium, which is used in conjunction with a phase transfer reagent (the phase transfer reagent therefore does not form a constituent of the catalyst system).

The reaction mixture comprises preferably two immiscible or poorly miscible liquid phases. One of the phases comprises substantially water (aqueous phase). In addition, this phase may comprise the peroxide, the catalyst system, phase transfer reagent and traces of the organic compound, and also conversion products thereof. The other phase (organic phase) typically comprises substantially the reaction product of the oxidation. In addition, this phase may comprise the organic compound, and also the catalyst system and the phase transfer reagent. In this respect, the reaction mixture is preferably a polyphasic system comprising an aqueous and an organic phase, in which a phase transfer reagent is also present. The catalysts described are often used in conjunction with a phase transfer reagent which makes it possible to transfer the inherently water-soluble catalyst into the organic phase.

Phase transfer reagents useful here include in particular ternary and quaternary ammonium compounds and also ester quats as described in EP-A-2946831 for example. Preference is given to amines or ammonium salts, wherein quaternary ammonium salts are particularly preferred. One example of a useful phase transfer reagent is the trioctylamine available under the name Alamine. The octyl radicals may have been at least partially replaced by decyl radicals. Examples of quaternary ammonium compounds are trialkylammonium methyl salts, wherein the alkyl chains each consist of six to twelve carbon atoms. Trialkylammonium methyl sulphate is an especially preferred phase transfer reagent of this invention.

The reaction rate of the oxidation is pH-dependent, if an aqueous phase is included. It is preferred in this respect that the oxidation is allowed to proceed at a pH≤4, preferably in a range from 1.5 to 4. The pH is adjusted preferably with at least one inorganic acid having a $pK_a$ (or a $pK_{a1}$) of 2.5 or less at 25° C. Suitable acids are selected from phosphoric acid, nitric acid, sulphuric acid, hydrochloric acid, perchloric acid and mixtures thereof, wherein preference is given to using phosphoric acid, sulphuric acid or mixtures thereof and particular preference is given to using sulphuric acid.

The oxidation may be carried out in an organic solvent. Alternatively, the oxidation can be carried out without solvent since the organic compound can itself function as solvent.

The catalyst system is reactivated by means of an aqueous base. Preferred bases are selected from ammonia, alkali metal hydroxides or mixtures thereof. Sodium and potassium are preferred alkali metals, wherein sodium is particularly preferred. Suitable bases are aqueous sodium hydroxide solution or aqueous potassium hydroxide solution. The solution of the base is added such that the desired pH is set. The catalyst is reactivated by a chemical reaction.

Before the reactivation is undertaken, the oxidized organic compound (product) and optionally the solvent can be separated from the catalyst system. The catalyst system is thereby concentrated. This can be effected for example by means of distillation, extraction, crystallisation or membrane filtration, wherein membrane filtration is preferred. Such separation methods are familiar to the person skilled in the art. With respect to membrane filtration, reference is made in particular to EP-A-2946831. Membrane filtration has the advantage that the reaction and reactivation can be carried out in the circuit as a continuous process. The concentrated catalyst system (retentate) is subsequently mixed with the aqueous base.

After the reactivation, the catalyst can be recycled to the reaction mixture (continuous procedure). Alternatively, the catalyst can be stored intermediately and can be used for later reactions (batch procedure), wherein a continuous procedure is preferred. The feeding can be carried out by recycling the phase in which the catalyst is located. The distribution of the metallic catalyst in the respective phases can be controlled by the pH.

After the reactivation and prior to the feeding to a reaction mixture, the pH is preferably adjusted in the resulting aqueous phase. This measure ensures that no decomposition of the peroxide, in particular the hydrogen peroxide, takes place in the reaction mixture. The pH should be adjusted advantageously in a range of <7, preferably 1.5-4. The pH is adjusted preferably with an inorganic acid having a $pK_a$ (or a $pK_{a1}$) of 2.5 or less at 25° C. Suitable acids are selected from phosphoric acid, nitric acid, sulphuric acid, hydrochloric acid and perchloric acid, wherein preference is given to phosphoric acid, sulphuric acid or mixtures thereof and particular preference is given to sulphuric acid. If the pH is adjusted, the catalyst system can be recycled to the reaction mixture. In this case it is advantageous to remove any organic phase which may be present.

Before the reaction mixture is fed to the membrane in the case of membrane filtration, if two liquid phases are present they are preferably separated. Said separation may be carried out using a phase separation vessel, for example. As such, the reaction mixture is introduced onto the membrane as a monophasic mixture rather than a biphasic mixture. It is preferable to subject the non-aqueous (organic) phase to membrane separation. The catalyst may also be removed from the aqueous phase using membrane technology. The aqueous and organic phases are thus freed of catalyst separately from one another using one membrane per phase. The membrane used for the aqueous phase may be different from the membrane used for the organic phase. The retentate comprising the catalyst-containing organic phase is subsequently fed to the reactivation.

The membrane used for the aqueous phase preferably comprises a membrane material selected from the following: polyamides, aromatic polyamides, polysulphones, polyethersulphones, hydrophobized polyethersulphones, sulphonated polyethersulphones, cellulose acetate, polypiperazine and polyvinylidene fluoride. By contrast, the organic phase should be separated preferably using a membrane based on silicone acrylate and/or polydimethylsiloxane (PDMS) and/or polyimide. The catalyst system concentrated from the two phases can be combined.

If reaction mixture phase separation were not to take place, a person skilled in the art is familiar with measures for achieving phase separation such as increasing the polarity of the aqueous phase or changing the density of one phase.

With the membrane method, the catalyst system is enriched in the retentate. The term "retentate" is understood by membrane specialists to mean the effluent from the membrane withdrawn upstream of the membrane. The material which passes through the membrane is known as "permeate" and is withdrawn downstream of the membrane. Here, the amount of catalyst retained may be established based on the amount of retained transition metal. The method in particular permits the retention in the retentate more than 50% of the transition metal based on the total amount of transition metal in the reaction mixture prior to filtration. The method preferably retains more than 70% of the transition metal, more preferably more than 90%. When a phase transfer reagent is employed, it will generally achieve a retention different from the transition metal. Said phase transfer reagent is nevertheless concentrated in the retentate. The entire catalyst system is therefore concentrated in the retentate at least to an extent. The transition metal may be detected using ICP-MS (inductively coupled plasma mass spectrometry) or XRF (X-ray fluorescence analysis).

FIGS. 1 to 4 illustrate the course of the process of a continuous procedure by means of membrane filtration. These process regimes represent particularly preferred embodiments of the invention. The organic compound V, preferably an unsaturated cyclic C6 to C12 compound, in particular CDEN, the peroxide X and the catalyst system C in the form of an aqueous solution are placed in a stirred tank (1) together with a phase transfer reagent. The pH is adjusted by means of an acid—if required—to a preferred value of ≤4. Stirred tank cascades are possible. The stirred tank(s) can be temperature controlled to temperatures of 20° C. to 150° C., whereupon the substances remain in the liquid state. In the phase separation vessel (2), the aqueous phase W1 is removed before the organic phase O1 is applied to the membrane (3). The oxidized product P can be separated as permeate. The catalyst system C in the organic phase O2 is passed into a further stirred tank (4) in which an aqueous base B, preferably aqueous sodium hydroxide solution, is added. The individual phases typically comprise:

W1: water, peroxide, catalyst system, phase transfer reagent

O1: organic compound, product, optionally organic solvent, catalyst system, phase transfer reagent O2: as O1, but higher concentration of catalyst system and lower concentration of product.

By separating the aqueous phase W1, a part of the catalyst system is removed from the process. This portion of the catalyst system can be partly recovered by a further base operation and can be fed back into the original method. For example, membranes in the aqueous phase are suitable for the purpose of partly retaining the catalyst system in the retentate. However, a part of the catalyst system is removed with the permeate from the process. The concentration of catalyst thereby decreases such that the conversion of the oxidation reaction may decrease. For this reason, fresh catalyst has to be added in order to at least keep the catalyst concentration constant in the reaction mixture.

In a first preferred variant (FIG. 1), the mixture of O2 and B is recycled to the stirred tank (1). If necessary, acid A is fed to the stirred tank (1) to adjust the pH.

In a second preferred variant (FIG. 2), the mixture of O2 and B is passed into a further stirred tank (5). There, the mixture is adjusted to the desired pH (preferably 1.5 to 4) with an inorganic acid A and recycled to the stirred tank (1).

In a third preferred variant (FIG. 3), the mixture of O2 and B is placed in a phase separation vessel (6), where the aqueous phase W2 is separated from the organic phase O3. W2 is fed into a stirred tank (7) into which the acid A which is introduced and which is adjusted to the desired pH (preferably 1.5 to 4). The mixture of W2 and A is recycled to the stirred tank (1) in the circuit.

W2: water, base, catalyst system

O3: as O2, but without catalyst system

Alternatively, the third variant can be carried out without membrane (3). Here, O1 is transferred directly into the stirred tank (4). The product remains in the organic phase and can be removed as O3.

Figure 4:
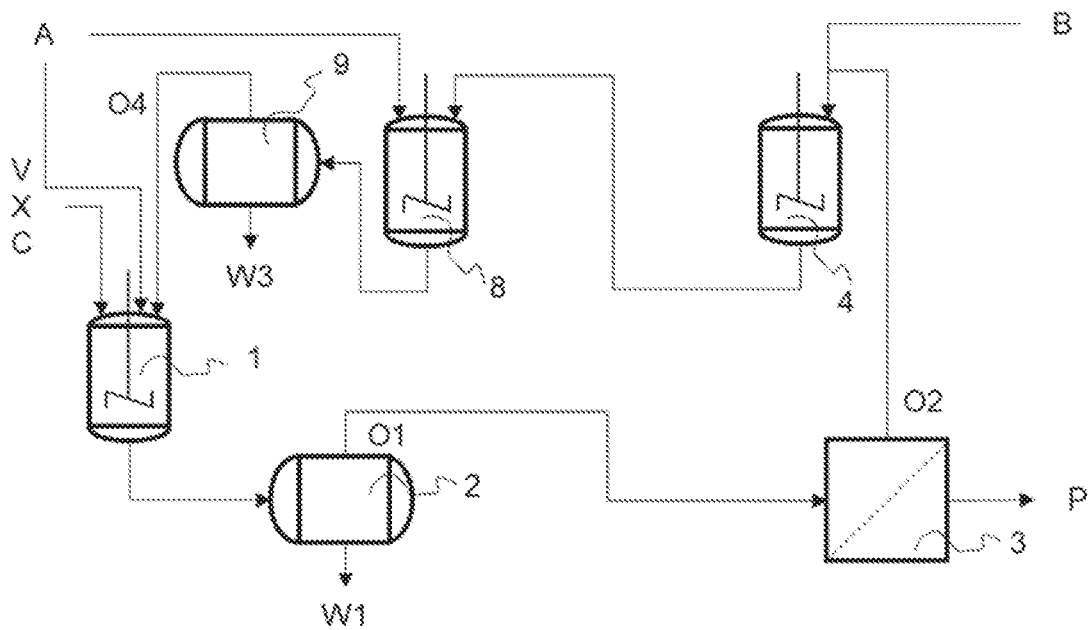

FIG. 4 demonstrates a fourth preferred variant, in which the mixture of O2 and B is transferred into a stirred tank (8) and is mixed with the acid A. The mixture is adjusted to the desired pH (preferably 1.5 to 4) with the acid. The resulting mixture of O2, B and A reaches a phase separation vessel (9), in which the aqueous phase W3 is removed and the remaining organic phase O4 is recycled to the stirred tank (1) in the circuit. By removal of the aqueous phase W3, further acid A can be passed into the stirred tank (1).

W4: water, salt of the inorganic acid and the base

O4: as O2.

The phases mentioned may comprise further constituents; in particular, separations are generally not effected quantitatively. The inorganic acid A is preferably selected from phosphoric acid, sulphuric acid and mixtures thereof, sulphuric acid being particularly preferred.

With the method according to the invention, it is possible to recover homogeneous catalysts after catalysis of oxidation reactions. This facilitates a particularly economical reaction regime since the catalyst can be recovered and reactivated. Addition of fresh catalyst is only required to a low degree.

The invention further relates to a method for the oxidation of organic compounds. In this case, a homogeneous oxidation catalyst system is used which has been reactivated by the method described above.

The catalyst system comprises at least one metal in its highest oxidation state, wherein the metal is selected from at least one metal of the IVb, Vb and VIb groups, and at least one phosphorus derivative. The catalyst system is reactivated by addition of at least one aqueous base at a pH≥4.5, preferably ≥7 and particularly ≥11.

The invention further relates to a method for the synthesis of lactams, preferably laurolactam (inventive lactam method). In a first stage, the organic compound in the form of a cyclic unsaturated compound, preferably C6 to C12 compound, preferably C12 compound, particularly preferably CDEN, is oxidized to the epoxide. The oxidation is effected in the presence of the homogeneous oxidation catalyst system which is reactivated by the method mentioned above.

The epoxidized compounds can subsequently be reacted, in the presence of a catalyst comprising a noble metal and a metal oxide, to the corresponding ketone. During the rearrangement or subsequent thereto, hydrogen can be added by which the alcohol derivative can be formed. If the ketone is present in a mixture with the alcohol derivative, a dehydrogenation of the alcohol to the ketone can take place. The ketone may subsequently be oximated. The Beckmann rearrangement to give the lactam may be carried out as a subsequent step using sulphuric acid or cyanuric chloride. The lactams may be subjected to further processing by polycondensation to give polyamides.

The rearrangement, the dehydrogenation, the oximation, the Beckmann rearrangement and the condensation reaction are known to a person skilled in the art.

In a preferred embodiment of the lactam method according to the invention, laurolactam is prepared from CDAN epoxide which reacts by polymerization to nylon 12.

In the context of the preferred lactam method, CDEN is obtainable by the following reaction steps: 1,3-butadiene is reacted to give cyclododecatriene by cyclotrimerization. This is followed by a hydrogenation to give the cyclododecene.

EXAMPLES

Example 1 (Non-Inventive)

Continuous Procedure without Reactivation

An epoxidation of cyclic unsaturated C12 compounds was carried out as a continuous operation in a 3 stage stirred tank cascade. The stirred tank cascade used comprised 2 reactors each having a 5 litre nominal capacity and, as a final stage, a stirred tank having a 25 litre nominal capacity. The three reactors comprised a jacket and were heated to a temperature of about 80° C. therewith.

The first reactor of the cascade was supplied with 2 kg/h of a cyclic unsaturated C12 compound (91% by weight CDEN and 9% by weight CDAN), trioctylammoniummethyl sulfate (as phase transfer reagent), sodium tungstate and phosphoric acid and a 50% $H_2O_2$ solution. In addition, a further quantity of $H_2O_2$ was metered into the second reactor. In total a ratio of 1.05 mol $H_2O_2$ per mol of CDEN was added.

The reaction mixture consisting of two liquid phases was passed from the cascade into a phase separation vessel from which the organic phase was supplied to a continuous membrane system using a pump.

The organic phase was fed at 45° C. through the membranes at a trans-membrane pressure difference of 41.5 bar and a cross flow rate of ca. 300 L/h. The membrane used was a polymer membrane from Evonik MET Ltd. with a nominal membrane surface area of 0.6 m=. The separation-active layer of the membranes consists of silicone acrylate and the carrier layer consists of polyimide.

83% of the feed to the membrane system was obtained as permeate. The retentate (17% of the feed to the membrane system), which comprises the catalyst system, was recycled into the reaction.

The aqueous phase from the phase separation vessel was likewise fed to a second continuous membrane system by means of a pump. The aqueous phase at 43° C. was fed through the membranes at a trans-membrane pressure difference of 40 bar and a cross flow rate of ca. 800 L/h. The membrane used was a thin layer composite polymer membrane Desal DK from GE Power & Water with a nominal membrane surface area of 0.7 m=. 55% of the feed to the membrane system was obtained as permeate. The retentate (45% of the feed to the membrane system), which comprises the catalyst system, was recycled into the first reactor of the cascade.

In addition to the recycling of the catalyst system with the retentate from the membrane system, phase transfer reagent, sodium tungstate and phosphoric acid were added to the first reactor. The amounts added are presented in the table below based on the CDEN amount in the feed.

|  | $Na_2WO_4$ | $H_3PO_4$ | Trialkylammoniummethyl sulfate |
|---|---|---|---|
| Amount based on the amount of CDEN fed | 0.9 mg/g | 3.4 mg/g | 2.2 mg/g |

With these catalyst characteristics, a conversion of the CDEN portion of 97% resulted after an operating time of 105 hours and a concentration of tungsten in the first reactor of the cascade of 0.45 mol % tungsten was determined by ICP mass spectrometry, based on CDEN in the feed.

After an operating time of the experimental system of 863 hours, a drop of the conversion of CDEN to 90% was observed. The concentration of tungsten in the first reactor of the cascade of 0.45 mol % tungsten was determined by ICP mass spectrometry, based on CDEN in the feed. Accordingly, a significantly poorer conversion resulted at the same tungsten concentration.

Example 2 (Non-Inventive)

Continuous Procedure without Reactivation

An epoxidation of cyclic unsaturated C12 compounds was carried out as a continuous operation in a 3 stage stirred tank cascade. The stirred tank cascade used comprised 2 reactors each having a 5 litre nominal capacity and, as a final stage, a stirred tank having a 25 litre nominal capacity. The three reactors comprised a jacket and were heated to a temperature of about 80° C. therewith.

The first reactor of the cascade was supplied with 1.5 kg/h of a cyclic unsaturated C12 compound (81% by weight CDEN and 19.1% by weight CDAN), Alamine (trioctylamine as phase transfer reagent), sodium tungstate and phosphoric acid and a 50% $H_2O_2$ solution. In addition, a further quantity of $H_2O_2$ was metered into the second reactor. In total a ratio of 1.08 mol $H_2O_2$ per mol of CDEN was added.

The reaction mixture consisting of two liquid phases was passed from the cascade into a phase separation vessel from which the organic phase was supplied to a continuous membrane system using a pump.

The organic phase was fed at 45° C. through the membranes at a trans-membrane pressure difference of 41.5 bar and a cross flow rate of ca. 300 L/h. The membrane used was a polymer membrane from Evonik MET Ltd. with a nominal membrane surface area of 0.6 m². The separation-active layer of the membranes consists of silicone acrylate and the carrier layer consists of polyimide.

79% of the feed to the membrane system was obtained as permeate. The retentate (21% of the feed to the membrane system), which comprises the catalyst system, was recycled into the reaction.

The aqueous phase from the phase separation vessel was likewise fed to a second continuous membrane system by means of a pump. The aqueous phase at 43° C. was fed through the membranes at a trans-membrane pressure difference of 40 bar and a cross flow rate of ca. 800 L/h. The membrane used was a thin layer composite polymer membrane Desal DK from GE Power & Water with a nominal membrane surface area of 0.7 m². 70% of the feed to the membrane system was obtained as permeate. The retentate (30% of the feed to the membrane system), which comprises the catalyst system, was recycled into the first reactor of the cascade.

In addition to the recycling of the catalyst system with the retentate from the membrane system, Alamine, sodium tungstate and phosphoric acid were added to the first reactor. The amounts added are presented in the table below based on the CDEN amount in the feed.

|  | Na$_2$WO$_4$ | H$_3$PO$_4$ | Alamine |
| --- | --- | --- | --- |
| Amount based on the amount of CDEN fed | 2.39 mg/g | 4.4 mg/g | 4.6 mg/g |

With these catalyst characteristics, a total conversion for the CDEN portion of 94.5% resulted.

After an operating time of the experimental system of 240 hours, a concentration of tungsten in the first reactor of the cascade of 1.08 mol % tungsten was determined by ICP mass spectrometry, based on CDEN in the feed. In addition, solid deposits were observed in the experimental system which led to blockage of the connecting lines between phase separation vessel and membrane system and further operation of the experimental system was no longer possible.

Example 3 (Inventive)

Continuous Method with Reactivation

Figure 2:
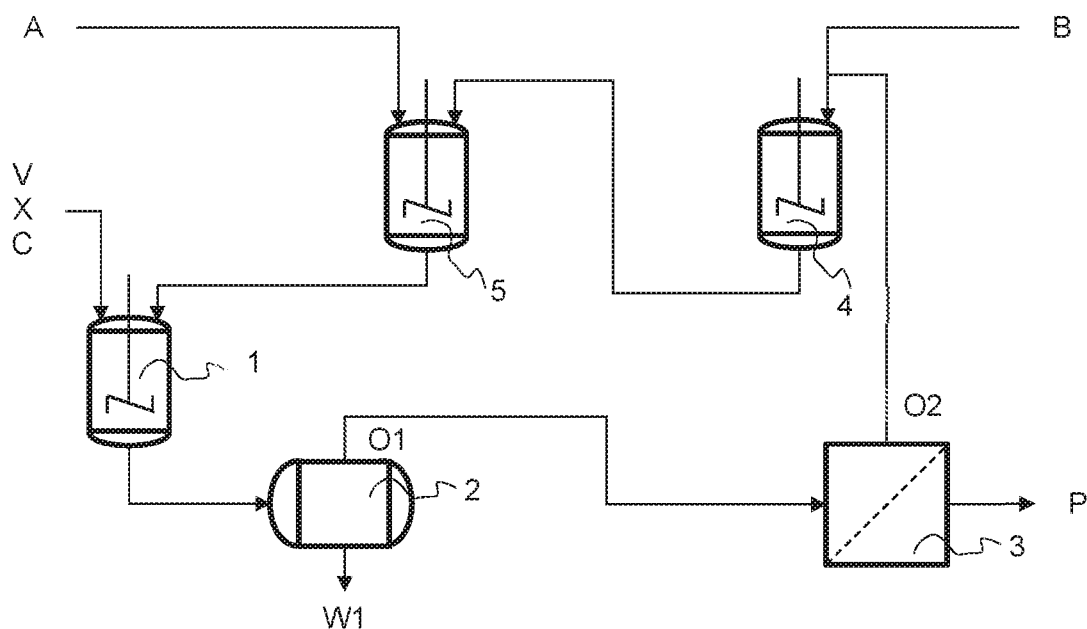
Figure 3:
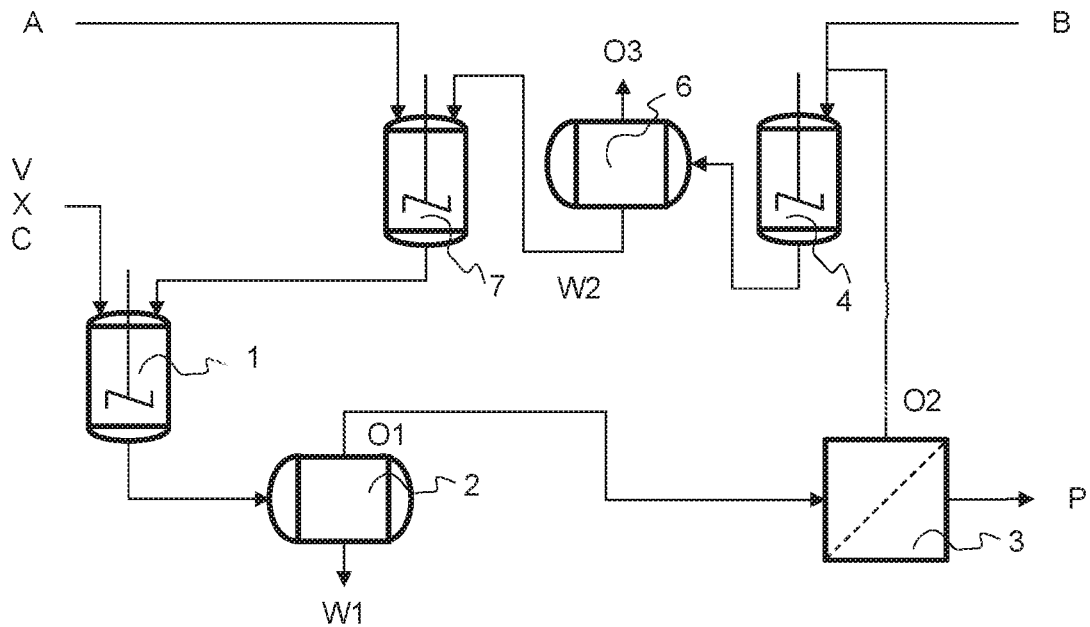

In the inventive example, the experimental set-up of Example 2 was supplemented by an alkali treatment for the retentate and a subsequent acid addition (analogous to FIG. 2).

The first reactor of the cascade was supplied with 2.3 kg/h of a cyclic unsaturated C12 compound (91% by weight CDEN and 9% by weight CDAN), Alamine (phase transfer reagent), sodium tungstate and phosphoric acid and a 50% H$_2$O$_2$ solution. In addition, a further quantity of H$_2$O$_2$ was metered into the second reactor. In total a ratio of 0.995 mol H$_2$O$_2$ per mol of CDEN was added.

The reaction mixture consisting of two liquid phases was passed from the cascade into a phase separation vessel from which the organic phase was supplied to a continuous membrane system using a pump.

The organic phase at 45° C. was fed through the membranes at a trans-membrane pressure difference of 41.5 bar and a cross flow rate of ca. 300 L/h. The membrane used was a polymer membrane from Evonik MET Ltd. with a nominal membrane surface area of 0.6 m$^2$. The separation-active layer of the membranes consists of silicone acrylate and the carrier layer consists of polyimide.

79% of the feed to the membrane system was obtained as permeate. The retentate (21% of the feed to the membrane system), which comprises the catalyst system, was fed into a further stirred tank, in which a 0.5M aqueous sodium hydroxide solution was added. The mixture was adjusted to a pH of 11. Subsequently the mixture was passed into a further stirred tank and there treated with sulphuric acid and adjusted to a pH of 2. The resulting mixture was recycled to the first reactor of the cascade.

The aqueous phase from the phase separation vessel was likewise fed to a second continuous membrane system by means of a pump. The aqueous phase at 43° C. was fed through the membranes at a trans-membrane pressure difference of 40 bar and a cross flow rate of ca. 800 L/h. The membrane used was a thin layer composite polymer membrane Desal DK from GE Power & Water with a nominal membrane surface area of 0.7 m². 70% of the feed to the membrane system was obtained as permeate. The retentate (30% of the feed to the membrane system), which comprises the catalyst system, was recycled into the first reactor of the cascade.

In addition to the recycling of the catalyst system, Alamine, sodium tungstate and phosphoric acid were added to the first reactor. The amounts added are presented in the table below based on the CDEN amount in the feed.

|  | Na$_2$WO$_4$ | H$_3$PO$_4$ | Alamine |
| --- | --- | --- | --- |
| Amount based on the amount of CDEN fed | 1.2 mg/g | 2.0 mg/g | 6 mg/g |

With these catalyst characteristics, a total conversion for the CDEN portion of 95% resulted.

After an operating time of the experimental system of 840 hours, a concentration of tungsten in the first reactor of the cascade of 0.51 mol % tungsten was determined by ICP mass spectrometry, based on CDEN in the feed. No solid deposits were observed in the experimental system which would force a shutdown of the experimental system.

Example 4 (Inventive)

Continuous Method with Reactivation

In the inventive example, the experimental set-up of Example 3 was supplemented by a phase separation after the alkali treatment of the retentate (analogous to FIG. 4). The organic phase from the additional phase separation was recycled into the reactor cascade. The aqueous phase was discharged from the process.

The first reactor of the cascade was supplied with 2.3 kg/h of a cyclic unsaturated C12 compound (91% by weight CDEN and 9% by weight CDAN), Alamine (phase transfer reagent), sodium tungstate and phosphoric acid and a 50% H$_2$O$_2$ solution. In addition, a further quantity of H$_2$O$_2$ was metered into the second reactor. In total a ratio of 0.979 mol H$_2$O$_2$ per mol of CDEN was added.

The reaction mixture consisting of two liquid phases was passed from the cascade into a first phase separation vessel from which the organic phase was supplied to a continuous membrane system using a pump.

The organic phase was fed at 45° C. through the membranes at a trans-membrane pressure difference of 41.5 bar and a cross flow rate of ca. 300 L/h. The membrane used was a polymer membrane from Evonik MET Ltd. with a nominal membrane surface area of 0.6 m$^2$. The separation-active layer of the membranes consists of silicone acrylate and the carrier layer consists of polyimide.

84% of the feed to the membrane system was obtained as permeate. The retentate (16% of the feed to the membrane system), which comprises the catalyst system, was fed into a further stirred tank, in which a 0.5M aqueous sodium hydroxide solution was added. The mixture was adjusted to a pH of 11. Subsequently the mixture was passed into a further stirred tank and there treated with sulphuric acid and adjusted to a pH of 2. Subsequently the mixture was fed to an additional phase separation vessel. The aqueous phase was discharged from the process. The resulting organic phase was recycled to the first reactor of the cascade.

The aqueous phase from the first phase separation vessel was likewise fed to a second continuous membrane system by means of a pump. The aqueous phase at 43° C. was fed through the membranes at a trans-membrane pressure difference of 40 bar and a cross flow rate of ca. 800 L/h. The membrane used was a thin layer composite polymer membrane Desal DK from GE Power & Water with a nominal membrane surface area of 0.7 m$^2$. 83% of the feed to the membrane system was obtained as permeate. The retentate (17% of the feed to the membrane system), which comprises the catalyst system, was recycled into the first reactor of the cascade.

In addition to the recycling of the catalyst system, Alamine, sodium tungstate and phosphoric acid were added to the first reactor. The amounts added are presented in the table below based on the CDEN amount in the feed.

|  | $Na_2WO_4$ | $H_3PO_4$ | Alamine |
|---|---|---|---|
| Amount based on the amount of CDEN fed | 1.2 mg/g | 3.5 mg/g | 4 mg/g |

With these catalyst characteristics, a total conversion for the CDEN portion of 91% resulted.

After an operating time of the experimental system of 500 hours, a concentration of tungsten in the first reactor of the cascade of 0.42 mol % tungsten was determined by ICP mass spectrometry, based on CDEN in the feed. No solid deposits were observed in the experimental system which would force a shutdown of the experimental system.

Example 5 (Inventive)

Continuous Method with Reactivation

In the inventive example, the experimental set-up of Example 3 was used.

The first reactor of the cascade was supplied with 2.0 kg/h of a cyclic unsaturated C12 compound (91% by weight CDEN and 9% by weight CDAN), trioctylammonium methyl sulphate (phase transfer reagent), sodium tungstate and phosphoric acid and a 50% $H_2O_2$ solution. In addition, a further quantity of $H_2O_2$ was metered into the second reactor. In total a ratio of 1 mol $H_2O_2$ per mol of CDEN was added.

The reaction mixture consisting of two liquid phases was passed from the cascade into a phase separation vessel from which the organic phase was supplied to a continuous membrane system using a pump.

The organic phase was fed at 45° C. through the membranes at a trans-membrane pressure difference of 41.5 bar and a cross flow rate of ca. 300 L/h. The membrane used was a polymer membrane from Evonik MET Ltd. with a nominal membrane surface area of 0.6 m². The separation-active layer of the membranes consists of silicone acrylate and the carrier layer consists of polyimide.

84% of the feed to the membrane system was obtained as permeate. The retentate (16% of the feed to the membrane system), which comprises the catalyst system, was fed into a further stirred tank, in which a 0.5M aqueous sodium hydroxide solution was added. The mixture was adjusted to a pH of 11. Subsequently the mixture was passed into a further stirred tank and there treated with sulphuric acid and adjusted to a pH of 2. The resulting mixture was recycled to the first reactor of the cascade.

The aqueous phase from the phase separation vessel was likewise fed to a second continuous membrane system by means of a pump. The aqueous phase at 43° C. was fed through the membranes at a trans-membrane pressure difference of 40 bar and a cross flow rate of ca. 800 L/h. The membrane used was a thin layer composite polymer membrane Desal DK from GE Power & Water with a nominal membrane surface area of 0.7 m². 55% of the feed to the membrane system was obtained as permeate. The retentate (45% of the feed to the membrane system), which comprises the catalyst system, was recycled into the first reactor of the cascade.

In addition to the recycling of the catalyst system, trioctylammonium methyl sulphate, sodium tungstate and phosphoric acid were added to the first reactor. The amounts added are presented in the table below based on the CDEN amount in the feed.

|  | $Na_2WO_4$ | $H_3PO_4$ | Trioctylammonium methyl sulphate |
|---|---|---|---|
| Amount based on the amount of CDEN fed | 0.6 mg/g | 3.5 mg/g | 1.6 mg/g |

With these catalyst characteristics, a total conversion for the CDEN portion of 95% resulted.

After an operating time of the experimental system of 790 hours, a concentration of tungsten in the first reactor of the cascade of 0.52 mol % tungsten was determined by ICP mass spectrometry, based on CDEN in the feed. No solid deposits were observed in the experimental system which would force a shutdown of the experimental system.

Comparison of the Examples

The examples 1-5 cited and the supplementary overview of the examples clarify the effectiveness of the invention.

Example 1 shows a non-inventive oxidation of cyclododecene with hydrogen peroxide in which the tungsten concentration was kept constant over the entire experimental period. The conversion achieved over the course of the experiment decreased significantly from 97% after 105 hours to 90% after 863 hours.

In example 5, in contrast, the catalyst was reactivated by adding aqueous sodium hydroxide solution to the retentate of the organophilic nanofiltration. After an operating time of 790 hours in example 5 with analogous operating conditions and analogous tungsten concentration, a significantly higher conversion of 95% could be observed.

Comparison of examples 1 and 5 shows that, after around 800 operating hours, a higher conversion of CDEN can be achieved with less $Na_2WO_4$ and less phase transfer catalyst if the catalyst is reactivated. In example 2, in a non-inventive embodiment as a major difference to example 1, alamine was used instead of trialkylammoniummethyl sulfate as phase transfer reagent. Without catalyst reactivation in example 2, a lot of fresh catalyst had to be added in order to achieve good conversions. A very high tungsten concentration was observed. In addition, solid deposits hampered the operation of the experimental plant and the experiment had to be aborted.

In example 3, in contrast to example 2, the catalyst was reactivated according to the invention by treating the retentate of the organophilic nanofiltration with aqueous sodium hydroxide solution. In contrast to example 2, with analogous phase transfer reagent, greater cydododecene throughput and longer experimental time, example 3 resulted in comparable conversions and thus a significantly higher space-time yield. At the same time, in example 3 less fresh catalyst was required and a very much lower tungsten concentration was found.

Example 4 illustrates a further embodiment of the invention—see FIG. 4. In example 4, in contrast to example 3, the water phase, which results from reactivation of the catalyst in the retentate of the organophilic nanofiltration with aqueous sodium hydroxide solution and subsequent adjustment of the pH with sulfuric acid, is removed and discharged from the process.

The comparison of examples 2 and 3 shows that more CDEN can be converted with less $Na_2WO_4$ if the catalyst is reactivated. The same applies to the comparison of examples 2 and 4. In addition, example 2 shows that the increased amount of catalyst which is needed to achieve the conversion without catalyst reactivation can lead to blockages and failure of the plant.

| Example | Cat reactivation | PTR | Set-up according to FIG. | Cat addition in mg/g | Operating hours | tungsten concentration measured | Conversion | particular incidents |
|---|---|---|---|---|---|---|---|---|
| 1* | no | TOAMS | — | 0.9 | 105 | 0.45% | 97% | |
| | | | | | 863 | 0.45% | 90% | |
| 2* | no | alamine | — | 2.4 | 240 | 1.08% | 94.5% | solid deposits |
| 3 | yes | alamine | 2 | 1.2 | 840 | 0.51% | 95% | |
| 4 | yes | alamine | 4 | 1.2 | 500 | 0.42% | 91% | |
| 5 | yes | TOAMS | 2 | 0.6 | 790 | 0.52% | 95% | |

*non-inventive cat = catalyst

PTR = phase transfer reagent

TOAMS = trioctylammoniummethyl sulfate

The invention claimed is:

1. A method for reactivating a catalyst system for epoxidizing an unsaturated organic compound in a reaction mixture, the method comprising:
   separating the catalyst system from an epoxidized organic compound in the reaction mixture prior to reactivating, and
   reactivating the catalyst system by adding at least one aqueous base at a pH≥4,
      wherein the reaction mixture comprises the catalyst system and at least one peroxide,
      the catalyst system is a homogeneous catalyst system for epoxidizing the unsaturated organic compound comprising at least one derivative of a metal in its highest oxidation state, wherein the derivative is at least one selected from the group consisting of $H_2WO_4$, $H_2MoO_4$, an alkali metal salt of $H_2WO_4$, an alkaline earth metal salt of $H_2WO_4$, an alkali metal salt of $H_2MoO_4$, an alkaline earth metal salt of $H_2MoO_4$, phosphoric acid, and a phosphoric acid salt.

2. The method according to claim 1, wherein the reaction mixture comprises an aqueous phase, an organic phase, and a phase transfer reagent.

3. The method according to claim 2, said reaction mixture is at a pH≤4.

4. The method according to claim 3, wherein the pH is ≤4, from at least one inorganic acid having a pKa (25° C.) of 2.5 or less.

5. The method according claim 2, wherein an organic phase is removed after the reactivating.

6. The method according to claim 1, wherein the pH of the catalyst system after the reactivating is adjusted to a value of <7.

7. The method according to claim 1, wherein the at least one peroxide is hydrogen peroxide.

8. The method according to claim 1, wherein the base is at least one selected from the group consisting of ammonia, alkali metal hydroxides, and any mixture thereof.

9. The method according to claim 8, wherein the base is at least one selected from the group consisting of sodium hydroxide and potassium hydroxide.

10. The method according to claim 1, wherein the organic compound is an unsaturated cyclic compound having six to twelve carbon atoms.

11. The method according to claim 1, wherein said reaction mixture does not contain an organic solvent.

12. A method for synthesizing a lactam, the method comprising:
   epoxidizing a cyclic unsaturated compound to an epoxide,
   rearranging the epoxide to a ketone,
      oximating the ketone to an oxime and
      rearranging the oxime to a lactam,
   wherein the cyclic unsaturated compound is epoxidized in the presence of a homogeneous oxidation catalyst system, and wherein a reactivation of the catalyst system is carried out according to claim 1.

13. A method for epoxidizing an unsaturated organic compound with a peroxide, the method comprising:
   epoxidizing the unsaturated organic compound with a homogeneous epoxidation catalyst system, which comprises at least one derivative of a metal in its highest oxidation state, in a reaction mixture, thereby obtaining an epoxidized organic compound,
   separating the catalyst system from the epoxidized organic compound, then
   reactivating the catalyst system by adding at least one aqueous base at a pH≥4, and
   recycling the catalyst system to the reaction mixture after reactivating,
   wherein the derivative is at least one selected from the group consisting of $H_2WO_4$, $H_2MoO_4$, an alkali metal salt of $H_2WO_4$, an alkaline earth metal salt of $H_2WO_4$, an alkali metal salt of $H_2MoO_4$, an alkaline earth metal salt of $H_2MoO_4$, phosphoric acid, and a phosphoric acid salt.

14. The method according to claim 13, wherein the catalyst system is reactivated by addition of at least one aqueous base at a pH≥4.5.

15. The method according to claim 14, wherein the catalyst system is reactivated by addition of at least one aqueous base at a pH≥7.

16. The method of claim 13, further comprising:
  maintaining a substantially constant concentration of the catalyst system in the reaction mixture.

\* \* \* \* \*